(12) United States Patent
Yip

(10) Patent No.: US 7,763,003 B1
(45) Date of Patent: Jul. 27, 2010

(54) DIAPER FOR CAPTURING AND ISOLATING BODILY WASTE

(75) Inventor: Jennifer Yip, Cornelius, NC (US)

(73) Assignee: Rhonda Yip, San Jose, CA (US)

( * ) Notice: Subject to any disclaimer, the term of this patent is extended or adjusted under 35 U.S.C. 154(b) by 524 days.

(21) Appl. No.: 11/508,095

(22) Filed: Aug. 21, 2006

(51) Int. Cl.
*A61F 13/15* (2006.01)
*A61F 13/20* (2006.01)

(52) U.S. Cl. ............... 604/385.19; 604/385.01; 604/385.101

(58) Field of Classification Search ........... 604/385.01, 604/385.04, 385.06, 385.09, 385.11, 385.13–385.14, 604/385.18–385.19
See application file for complete search history.

(56) References Cited

U.S. PATENT DOCUMENTS

| | | | | |
|---|---|---|---|---|
| 2,749,558 A | * | 6/1956 | Lent et al. | 4/454 |
| 4,210,143 A | * | 7/1980 | De Jonckheere | 604/389 |
| 4,560,380 A | * | 12/1985 | Tharel | 604/385.19 |
| 4,623,339 A | * | 11/1986 | Ciraldo et al. | 604/359 |
| 4,772,282 A | * | 9/1988 | Oakley | 604/385.03 |
| 4,834,737 A | * | 5/1989 | Khan | 604/385.14 |
| 4,964,857 A | * | 10/1990 | Osborn | 604/395 |
| 5,304,160 A | * | 4/1994 | Igaue et al. | 604/385.28 |
| 6,516,588 B2 | * | 2/2003 | Jensen et al. | 53/459 |
| 2005/0038400 A1 | * | 2/2005 | Poruthoor | 604/385.01 |

FOREIGN PATENT DOCUMENTS

GB  2 001 236 A  *  1/1979
WO  98/29080  *  7/1998

* cited by examiner

*Primary Examiner*—Michele Kidwell
(74) *Attorney, Agent, or Firm*—Schwartz Law Firm, P.C.

(57) ABSTRACT

A diaper is adapted for capturing and isolating bodily waste of a wearer. The diaper is constructed of a fabric blank folded to form front and rear waistlines of the diaper, a crotch region located between the front and rear waistlines, and a pair of leg openings. The fabric blank includes an outside shell and an adjustable inside panel. The inside panel is movable during wear from a normal wear position, wherein the crotch region is substantially uncovered by the panel, to a waste-isolating position, wherein the crotch region is substantially covered by the panel.

16 Claims, 4 Drawing Sheets

DIAPER FOR CAPTURING AND ISOLATING BODILY WASTE

TECHNICAL FIELD AND BACKGROUND OF THE INVENTION

This invention relates to a diaper adapted for capturing and isolating bodily waste. The invention incorporates novel features which serve to substantially isolate bodily fluids and excretions from the skin of the wearer until the diaper can be changed.

SUMMARY OF THE INVENTION

Therefore, it is an object of the invention to provide a diaper for capturing and isolating bodily waste including bodily fluids and excretions.

It is another object of the invention to provide a diaper which can be manufactured in a variety of sizes and styles, and which is applicable for wear by individuals of all ages including infants and elderly adults.

It is another object of the invention to provide a diaper which is either disposable, or launderable and reusable.

These and other objects of the present invention are achieved in the preferred embodiments disclosed below by providing a diaper adapted for capturing and isolating bodily waste of a wearer. The term "diaper" is defined broadly herein to mean any launderable, reusable, or disposable garment, wrap, covering, or the like adapted for wear by infants, children and/or adults. The diaper is constructed of a fabric blank folded to form front and rear waistlines of the diaper, a crotch region located between the front and rear waistlines, and a pair of leg openings. The fabric blank comprises an outside shell and an adjustable inside panel. The inside panel is movable during wear from a normal wear position, wherein the crotch region is substantially uncovered by the panel, to a waste-isolating position, wherein the crotch region is substantially covered by the panel. Bodily waste passes from the wearer to the crotch region of the diaper with the adjustable inside panel in the normal wear position. The bodily waste is subsequently substantially isolated from the wearer by moving the inside panel from the normal wear position to the waste-isolating position, such that the bodily waste resides substantially between the inside panel and the outside shell.

According to one preferred embodiment of the invention, a drawstring is attached to the adjustable inside panel, and is adapted for being grasped and pulled to move the inside panel from the normal wear position to the waste-isolating position.

Preferably, the drawstring extends from the adjustable inside panel through an opening formed with the outside shell to an outside of the diaper.

According to another preferred embodiment of the invention, a waste-collection pouch is located at the crotch region and formed with the outside shell to capture bodily waste passing from the wearer into the diaper.

Preferably, means are provided for closing the waste-collection pouch to further isolate the bodily waste.

According to one preferred embodiment of the invention, the means for closing the waste-collection pouch comprises a drawstring.

According to another preferred embodiment of the invention, at least one fastener tab is provided for releasably attaching the front and rear waistlines together.

Preferably, the inside panel comprises a hydrophobic fibers.

Preferably, the outside shell comprises a liquid impermeable fabric.

In another embodiment, the invention is a diaper for capturing and isolating bodily waste of a wearer. The diaper is constructed of a fabric blank folded to form front rear waistlines of the diaper, a crotch region located between the front and rear waistlines, and a pair of leg openings. The fabric blank comprises an outside shell and first and second cooperating adjustable inside panels. The inside panels are movable during wear from a normal wear position, wherein the crotch region is substantially uncovered by the panels, to a waste-isolating position, wherein the crotch region is substantially covered by the panels. Bodily waste passes from the wearer to the crotch region of the diaper with the adjustable inside panels in the normal wear position. The bodily waste is subsequently substantially isolated from the wearer by moving the inside panels from the normal wear position to the waste-isolating position, such that the bodily waste resides substantially between the inside panels and the outside shell.

In yet another embodiment, the invention is a diaper adapted for capturing and isolating bodily waste of a wearer, and including an outside shell fabric. The shell fabric comprises front and rear waistlines, a crotch region located between the front and rear waistlines, and a pair of leg openings. An adjustable inside panel is located inside of the shell fabric. The inside panel is movable during wear from a normal wear position, wherein the crotch region is substantially uncovered by the panel, to a waste-isolating position, wherein the crotch region is substantially covered by the panel. Bodily waste passes from the wearer to the crotch region of the diaper with the adjustable inside panel in the normal wear position. The bodily waste is subsequently substantially isolated from the wearer by moving the inside panel from the normal wear position to the waste-isolating position, such that the bodily waste resides substantially between the inside panel and the outside shell.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be operative, enabling, and complete. Like numbers refer to like elements throughout. Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described.

Figure 1:
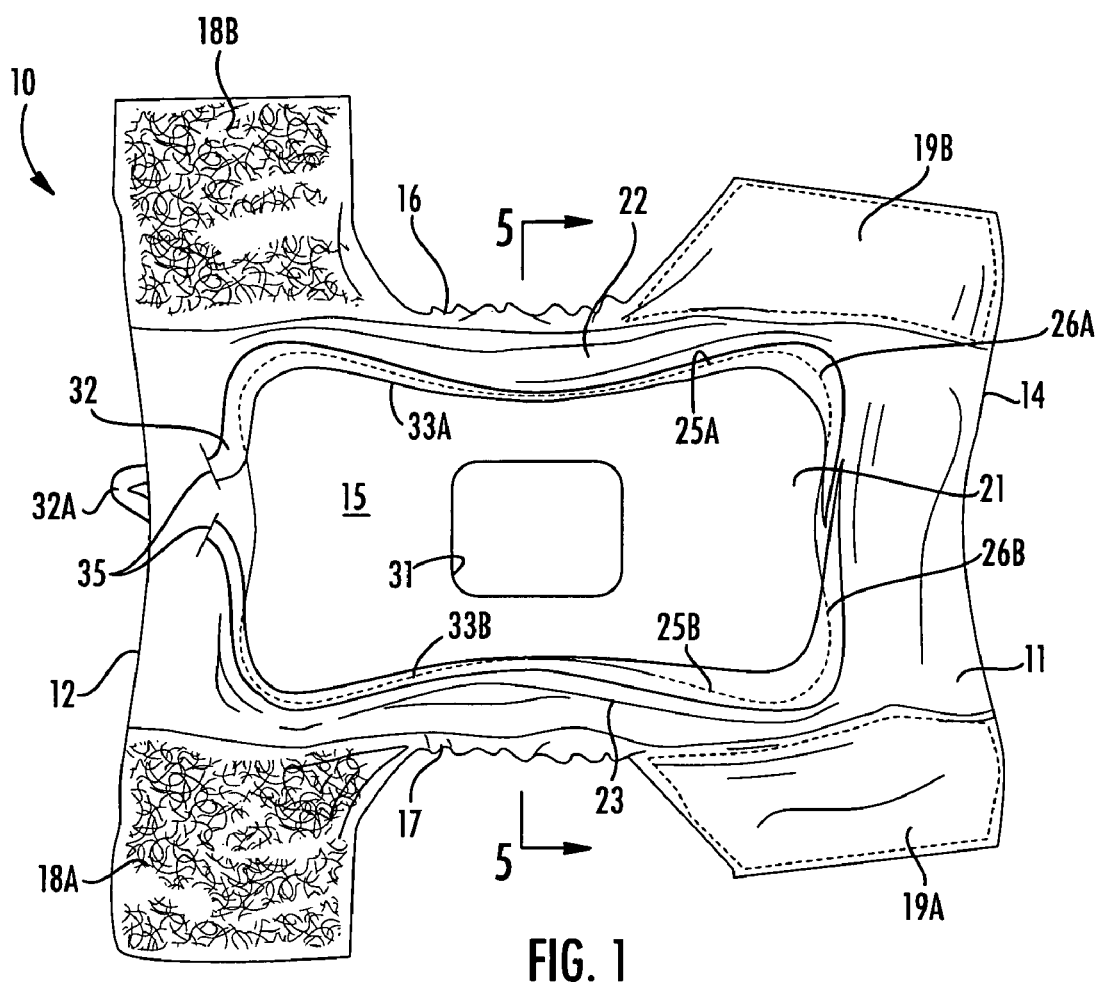
FIG. 1 is a view illustrating an inside of the diaper according to one preferred embodiment of the present invention, and showing the adjustable panels in a normal wear position.

Referring now specifically to the drawings, a diaper according to the present invention is illustrated in FIG. 1, and shown generally at reference numeral 10. In the embodiment shown, the diaper 10 comprises a disposable (or launderable) fabric blank 11 which is folded and applied to the wearer in a conventional manner—i.e., as standard commercially-available diapers are generally applied to infants. The folded blank 11 defines front and rear waistlines 12 and 14, a crotch region 15 extending between the waistlines, and a pair of leg openings 16 and 17. Respective tabs 18A, 18B and 19A, 19B extending from the waistlines 12, 14 have complementary hook and loop fasteners or other attachment means which mate to releasably secure the diaper 10 to the wearer. In an alternative embodiment (not shown), the diaper may be constructed in an integrally-formed brief, boxer, or boxer-brief style for both men and women.

Figure 5:
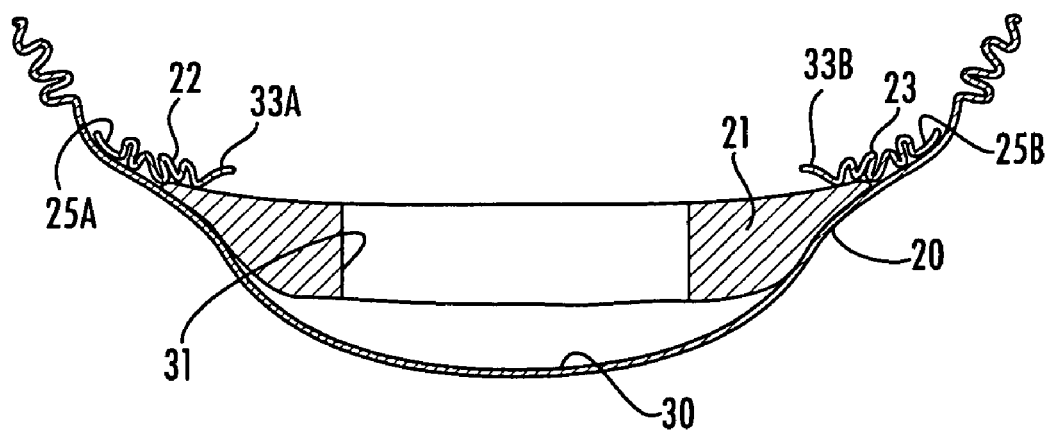
FIG. 5 is a cross-sectional view taken substantially along line 5-5 of FIG. 1.
Figure 6:
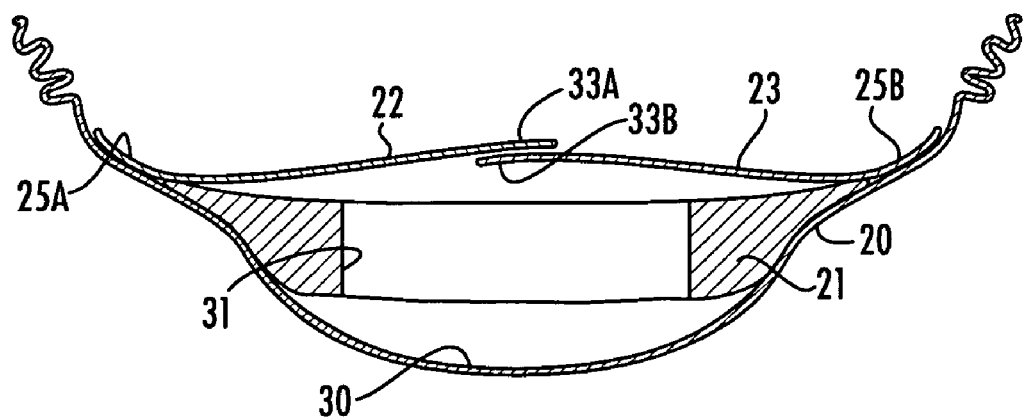
FIG. 6 is a cross-sectional view taken substantially along line 6-6 of FIG. 3.

The fabric blank 11 comprises an outside shell fabric 20 (See FIGS. 4-6), one or more adjacent inner fabric layers 21, and first and second adjustable inside panels 22 and 23. Preferably, the shell fabric 20 comprises an outermost layer of moisture-impermeable material. The inner layers 21 are constructed of highly absorbent fibers in the crotch region of the diaper 10, and may be either separately formed or integrally-formed with the outside shell fabric 20.

The adjustable panels 22, 23 are located in the crotch region 15, and are attached to the shell fabric 20 along respective longitudinal outside edges 25A, 25B and lateral end edges 26A, 26B. The panels 22, 23 are preferably constructed of a hydrophobic or moisture-impermeable fabric. In a normal wear position, shown in FIGS. 1 and 5, the adjustable panels 22, 23 reside substantially along an outer periphery of the crotch region 15 and in a generally compressed condition. In this position, the panels 22, 23 provide substantially unobstructed access to a waste-collection pouch 30 formed with the outside shell fabric 20 (See FIGS. 4-6). Access to the collection pouch 30 is defined by an enlarged opening 31 formed with the absorbent layer 21 and centrally located in the crotch region 15 of the diaper 10. A drawstring 32 extends along respective unattached inside edges 33A, 33B of the panels 22, 23, and passes from inside of the diaper 10 to the outside through small holes 35 formed with the outside shell fabric 20. Preferably, a looped portion 32A of the drawstring 32 is readily accessible from outside the diaper 10.

Figure 2:
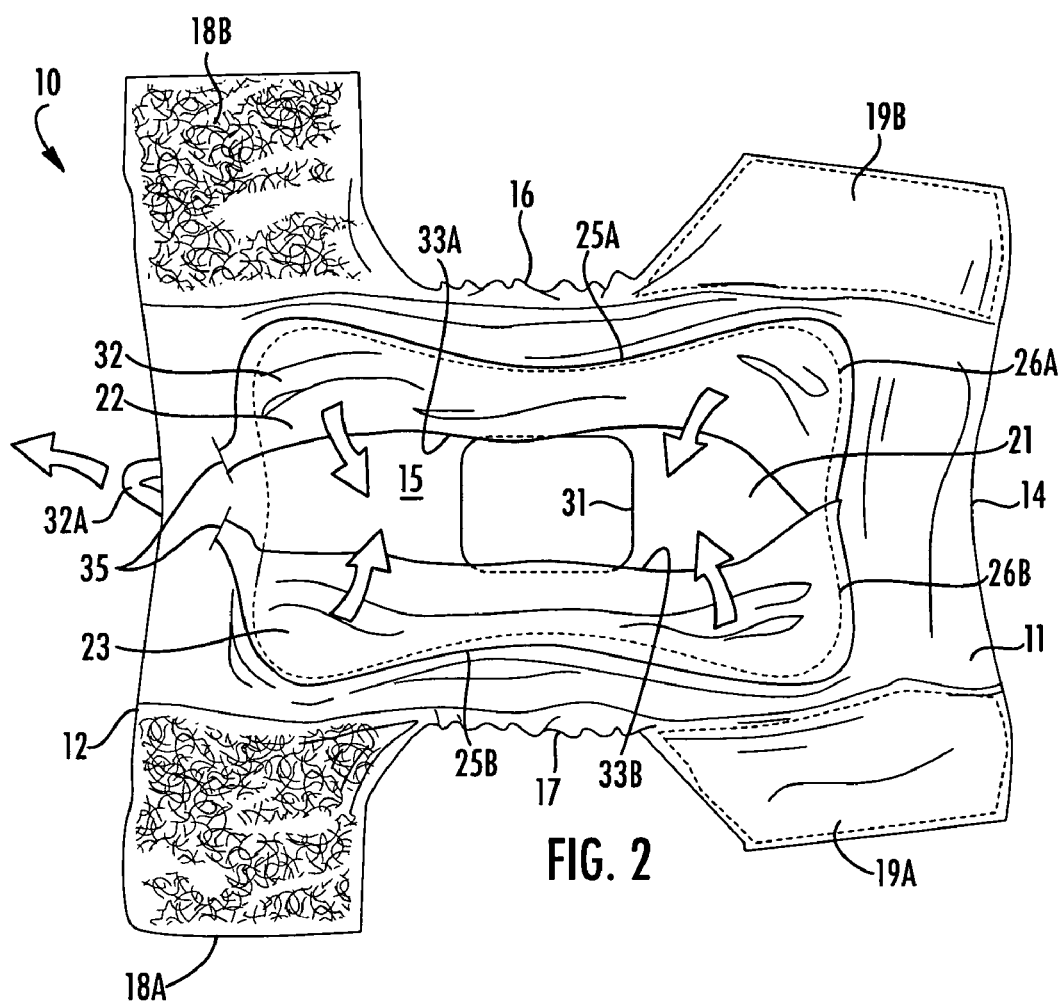
FIG. 2 is another view illustrating the inside of the diaper, and demonstrating movement of the adjustable panels from the normal wear position to the waste-isolating position.
Figure 3:
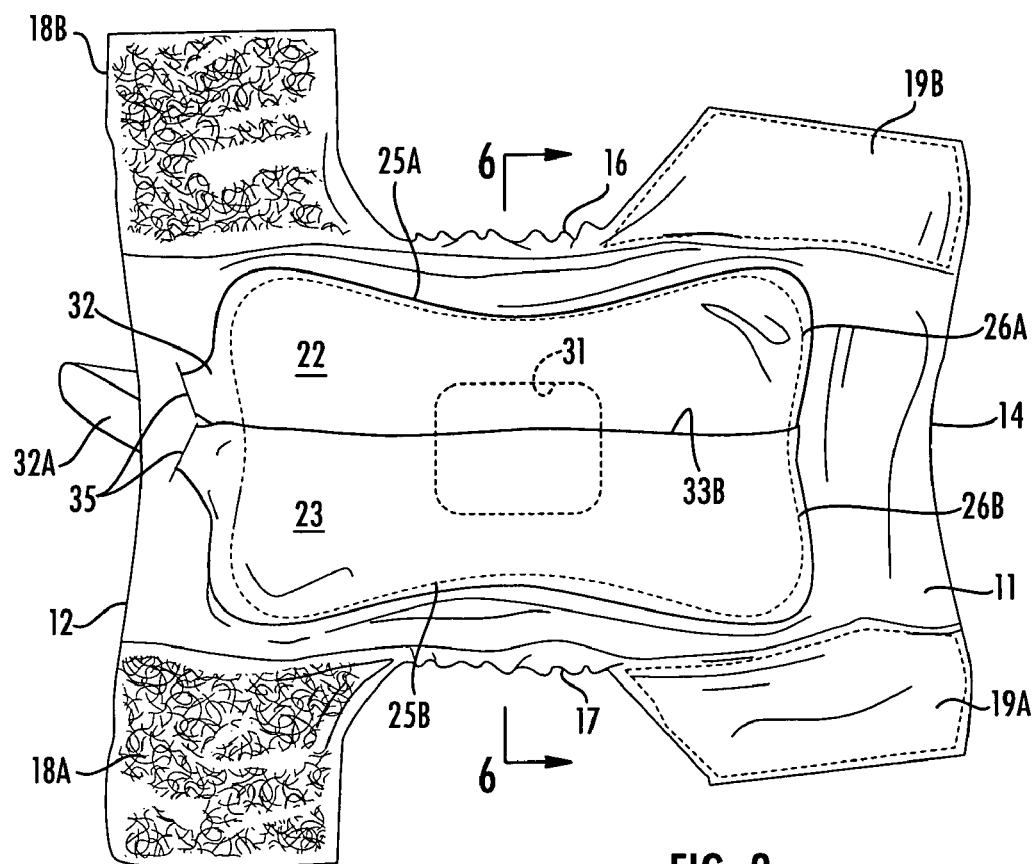
FIG. 3 is yet another view illustrating the inside of the diaper, and showing the adjustable panels in the waste-isolating position.

As bodily waste passed from the wearer into the diaper 10 it enters the collection pouch 30 through the opening 31. Subsequently, the captured bodily waste is isolated from the wearer by manually pulling the looped portion 32A of the drawstring 32, as demonstrated in FIG. 2, thereby moving the adjustable inside panels 22, 23 from their normal wear position to a waste-isolating position. In the waste-isolating position, shown in FIGS. 3 and 6, the adjustable panels 22, 23 curtain inwardly and overlap along their respective unattached inside edges 33A, 33B to substantially close off the opening 31 to the collection pouch 30. The captured bodily waste resides substantially between the closed inside panels 22, 23 and the outside shell fabric 20, and away from the skin of the wearer. To promote more complete closure of the opening 31, the panels 22, 23 preferably overlap slightly along their attached end edges 26A, 26B. Additionally, complementary attachment means (e.g., hook and loop fasteners) may be located on contacting surfaces of the overlapping edges 33A, 33B to attach the panels 22, 23 together once the opening 31 is closed.

Figure 4:
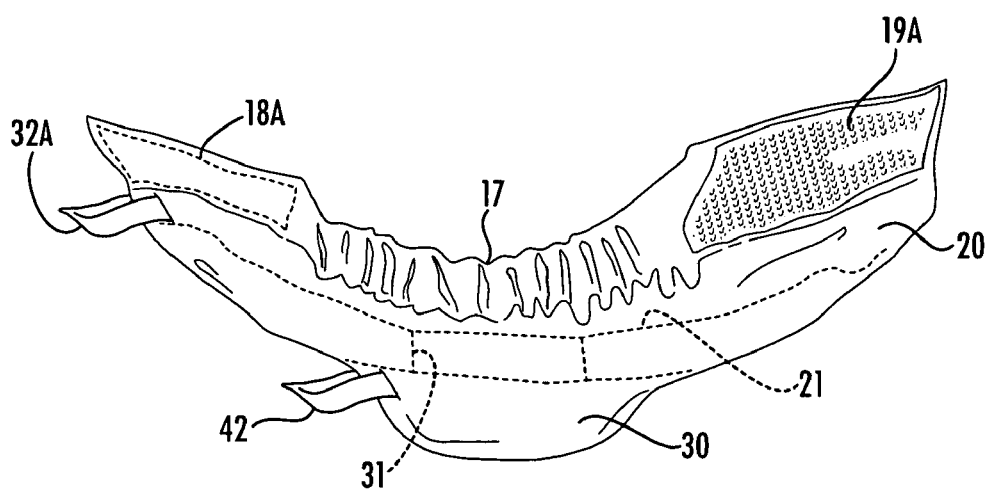
FIG. 4 is a side view of the diaper.

As a further means of isolating the bodily waste, a second drawstring 42 shown in FIG. 4 may extend along an inside periphery of the collection pouch 30 adjacent the opening 31. Like drawstring 32, the drawstring 42 passes from inside the diaper 10 to the outside through small holes 43 formed with the outside shell fabric 20, and has a looped portion which is readily accessible from outside the diaper 10. When manually pulled, the drawstring 42 operates to further close-off the opening 31.

One or both drawstrings 32, 42 may be manually pulled while the diaper 10 is in place on the wearer to limit direct contact of bodily waste with the skin prior to replacing the diaper 10. Alternatively, one or both drawstrings 32, 42 may be pulled only after the diaper 10 is removed from the wearer—as a means to facilitate handling and/or disposal. The drawstrings 32, 42 may be pulled by the wearer, a parent, or other caregiver. The diaper 10 may be made in a variety of sizes, and is applicable for wear by individuals of all ages.

A diaper is described above. Various details of the invention may be changed without departing from its scope. Furthermore, the foregoing description of the preferred embodiment of the invention and best mode for practicing the invention are provided for the purpose of illustration only and not for the purpose of limitation—the invention being defined by the claims.

I claim:

1. A diaper adapted for capturing and isolating bodily waste of a wearer, said diaper comprising:
   a multiple layer fabric blank folded to form front and rear waistlines of said diaper, a crotch region located between the front and rear waistlines, and a pair of leg openings;
   said fabric blank comprising an outside shell, a collection pouch within said crotch region, and first and second cooperating adjustable inside panels, said first and second inside panels having respective outside edges attached to said outside shell and opposing unattached inside edges, and said first and second inside panels being movable during wear from a normal wear position to a waste-isolating position, wherein in the normal wear position said first and second inside panels define substantially unobstructed access to said collection pouch between said opposing unattached inside edges, and wherein in the waste-isolating position said first and second inside panels curtain inwardly and overlap along their respective unattached inside edges to substantially close access to said collection pouch.

2. A diaper according to claim 1, and comprising a drawstring attached to said first and second adjustable inside panels, and adapted for being grasped and pulled to move said inside panels from the normal wear position to the waste-isolating position.

3. A diaper according to claim 2, wherein said drawstring extends from said first and second inside panels through an opening formed with said outside shell to an outside of said diaper.

4. A diaper according to claim 2, and comprising means for closing said waste-collection pouch to further isolate the bodily waste.

5. A diaper according to claim 4, wherein said means for closing said waste-collection pouch comprises a drawstring.

6. A diaper according to claim 1, and comprising at least one fastener tab adapted for releasably attaching the front and rear waistlines together.

7. A diaper according to claim 1, wherein said inside panel comprises hydrophobic fibers.

8. A diaper according to claim 1, wherein said outside shell comprises a liquid impermeable fabric.

9. A diaper adapted for capturing and isolating bodily waste of a wearer, said diaper comprising:
- an outside shell fabric comprising front and rear waistlines, a crotch region located between the front and rear waistlines, and a pair of leg openings;
- a collection pouch adjacent said crotch region; and
- first and second adjustable inside panels located inside of said shell fabric and having respective outside edges attached to said shell fabric and opposing unattached inside edges, and said first and second inside panels being movable during wear from a normal wear position to a waste-isolating position, wherein in the normal wear position said first and second inside panels define substantially unobstructed access to said collection pouch between said opposing unattached inside edges, and wherein in the waste-isolating position said first and second inside panels curtain inwardly and overlap along their respective unattached inside edges to substantially close access to said collection pouch.

10. A diaper according to claim 9, and comprising a drawstring attached to said first and second adjustable inside panels, and adapted for being grasped and pulled to move said inside panels from the normal wear position to the waste-isolating position.

11. A diaper according to claim 10, wherein said drawstring extends from said first and second inside panels through an opening formed with said outside shell fabric to an outside of said diaper.

12. A diaper according to claim 10, and comprising means for closing said waste-collection pouch to further isolate the bodily waste.

13. A diaper according to claim 12, wherein said means for closing said waste-collection pouch comprises a drawstring.

14. A diaper according to claim 9, and comprising at least one fastener tab adapted for releasably attaching the front and rear waistlines together.

15. A diaper according to claim 9, wherein said first and second inside panels comprise hydrophobic fibers.

16. A diaper according to claim 9, wherein said outside shell fabric comprises a liquid impermeable fabric.

\* \* \* \* \*